US United States Patent [19]

Reading

[11] Patent Number: 4,714,681

[45] Date of Patent: * Dec. 22, 1987

[54] QUADROMA CELLS AND TRIOMA CELLS AND METHODS FOR THE PRODUCTION OF SAME

[75] Inventor: Christopher L. Reading, Kingwood, Tex.

[73] Assignee: The Board of Reagents, The University of Texas System Cancer Center, Austin, Tex.

[*] Notice: The portion of the term of this patent subsequent to Oct. 2, 2001 has been disclaimed.

[21] Appl. No.: 621,394

[22] Filed: Jun. 18, 1984

Related U.S. Application Data

[63] Continuation of Ser. No. 279,248, Jul. 1, 1981, Pat. No. 4,474,893.

[51] Int. Cl.$^4$ .................. C12N 5/00; C12N 15/00; C07K 15/04
[52] U.S. Cl. .................. 435/240.27; 435/68; 435/70; 435/172.2; 435/948; 436/548; 935/90; 935/92; 935/93; 935/95; 935/100; 935/104; 935/107; 935/108; 935/110
[58] Field of Search .................. 435/240, 241, 68, 70, 435/935, 172.2; 436/548; 935/89, 90, 92, 93, 95, 99, 100, 102, 103, 104, 107, 108, 110

[56] References Cited

U.S. PATENT DOCUMENTS

| | | | |
|---|---|---|---|
| 4,172,124 | 10/1979 | Koprowski | 424/85 |
| 4,196,265 | 4/1980 | Koprowski | 424/85 |
| 4,350,683 | 9/1982 | Galfre | 424/85 |
| 4,444,878 | 4/1984 | Paulus | 435/188 |
| 4,474,893 | 10/1984 | Reading | 436/547 |
| 4,529,694 | 7/1985 | Lazarus et al. | 435/240 |

FOREIGN PATENT DOCUMENTS

| | | |
|---|---|---|
| 68763 | 1/1983 | European Pat. Off. |
| 83/00525 | 4/1983 | PCT Int'l Appl. |

OTHER PUBLICATIONS

Milstein, C. et al., Nature, vol. 305, pp. 537-540, (10-1983).
Sikora, K. et al., Blood, vol. 54 (2), pp. 513-518, (8-1979).
Levy, R. et al., Proc. Natl. Acad. Sci., USA, vol. 75 (5), pp. 2411-2415, (5-1978).
Howard, J. et al., Immunol. Reviews, vol. 47, pp. 140-174, (1979): see pp. 150-153.
Martinis, J. et al., Protides Biological Fluids Proc. Coll., vol. 30, pp. 311-316, Pergamon Press, Oxford (1983).
Reading, C. L., J. Immunological Methods, vol. 53/31, pp. 261-292, (1982).
Cotton, R. G. H. et al., Nature, vol. 244, pp. 42-43, (7-1973).
Schwaker, J. et al., Proc. Natl. Acad. Sciences, vol. 71 (6), pp. 2203-2207, (6-1974).
Raschke, William C., Bioch. Biophys. Acta., vol. 605 (1), pp. 114-125, (3-1980).
Yelton, D. E. et al., *Plasmacytomas and Hybridomas*, pp. 3-17, (1980).
Yelton, D. E. et al., Transplantation Proceedings, vol. 12, (3), pp. 439-442 (1980).
Kohler, G. et al., European J. Immunology, vol. 6, pp. 511-519, (1976).
Gefter, M. L. et al., Somatic Cell Genetics, pp. 231-236, (1977).
Schwaker, J., Somatic Cell Genetics, vol. 3 (3), pp. 295-302, (1977).
Laskov, R. et al., Proc. Natl. Acad. Sci., USA, vol. 76, (2), pp. 915-919 (1979).
Hammerling, V. et al., J. Experimental Medicine, vol. 128, pp. 1461-1469.
Kohler, G. et al., Nature, vol. 256, pp. 495-497 (1975).
Margulies, D. H. et al., Cell, vol. 8, pp. 405-415, (1976).
Kranz, D. M. et al., Proc. Natl. Acad. Sci., USA, vol. 78, pp. 5807-5812 (1981).

*Primary Examiner*—Margaret Moskowitz
*Attorney, Agent, or Firm*—Sughrue, Mion, Zinn, Macpeak & Seas

[57] ABSTRACT

Antibodies having binding affinity for two desired antigens, hereinafter "recombinant monoclonal antibodies"; recombinant monoclonal antibodies produced by a quadroma cell or a trioma cell; and methods for producing recombinant monoclonal antibodies by means of a quadroma cell or a trioma cell, wherein a quadroma cell is the fusion product of a hybridoma cell which produces an antibody having specific binding affinity to one desired antigen and a hybridoma cell which produces an antibody having specific binding affinity for another desired antigen, and wherein a trioma cell is the fusion product of a hybridoma cell which produces an antibody having specific binding affinity to one desired antigen and a lymphocyte which produces an antibody having specific binding affinity to another desired antigen.

56 Claims, No Drawings

QUADROMA CELLS AND TRIOMA CELLS AND METHODS FOR THE PRODUCTION OF SAME

BACKGROUND AND PRIOR ART

The present invention relates to the field of monoclonal antibodies. In particular, the invention relates to the creation of new biological entities termed triomas and quadromas, which produce new bifunctional antibodies termed recombinant monoclonal antibodies herein. Recombinant monoclonal antibodies (hereinafter designated RMA) have a wide range of diagnostic and therapeutic uses, to be described in detail herein.

Antibodies are normally synthesized by lymphoid cells derived from B lymphocytes of bone marrow. The great diversity of antibody specificities is accomplished by immunoglobulin molecules having many structural features in common. Individual antibody molecules of heterogeneous binding specificity differ in their detailed amino acid sequences and even antibodies of the same specificity are usually a mixture of immunoglobulins having different amino acid sequences, although such sequences may be substantially homologous. The terms "antibody" and "immunoglobulin" are used interchangeably herein.

Individual lymphocytes produce immunoglobulin of a single amino acid sequence. Lymphocytes cannot be directly cultured to produce their specific antibody. However, Kohler, et al, *Nature* 256, 495 (1975) demonstrated that a process of somatic cell fusion, specifically between a lymphocyte and a myeloma cell, could yield hybrid cells which grow in culture and produce a specific antibody. Myeloma cells are lymphocyte tumor cells which, depending upon the cell strain, frequently produce an antibody themselves, although some "non-producing" strains are known.

The hybrid resulting from somatic fusion of a lymphocyte and a myeloma cell is termed a "hybridoma" cell herein and in the art generally. In a typical fusion procedure, spleen lymphocytes from an animal immunized against a chosen antigen are fused with myeloma cells. The resulting hybridomas are then dispersed in a series of separate culture tubes or microtitre plate wells to screen for cultures producing a desired antibody. Positive cultures are further diluted to obtain colonies arising from a single cell (clones). The clones are again screened for production of the desired antibody. Antibody produced by a cloned hybridoma is termed "monoclonal" herein and in the art.

From genetic studies with lymphocytes and hybridomas, it is known that specific antibodies are coded by DNA segments that are selected from a variety of possible coding segments originally present in germ line cells. As differentiation proceeds, some of the coding segments are rearranged or deleted, so that fully differentiated lymphocytes are genetically restricted to production of a single antibody. See *Science* 212, 1015 (1981). Previous attempts to demonstrate synthesis of more than one antibody by a single cell or clone have been successful only to the extent that myeloma-myeloma fusion cells have been shown to produce mixed myeloma proteins (Cotton, R. G. H., et al, *Nature* 244, 42 (1973)).

Monoclonal antibodies are highly specific, being directed against a single antigen only. Furthermore, in contrast to conventional antibody preparations which typically include different antibodies directed against different sets of determinants on the same antigen, monoclonal antibodies are directed only against a single determinant on the antigen. Monoclonal antibodies are useful to improve the selectivity and specificity of diagnostic and analytical assay methods using antigen-antibody binding. A second advantage of monoclonal antibodies is provided by the fact that they are synthesized in pure form by the hybridoma culture, uncontaminated by other immunoglobulins. Monoclonal antibodies may be prepared from supernatants of cultured hybridoma cells or from ascites induced by intraperitoneal inoculation of hybridoma cells into mice.

The immunoglobulin protein structure is well known. Immunoglobulin G (IgG) consists of two heavy protein chains (molecular weight ~64,000) and two light protein chains (molecular weight ~22,500). The heavy chains are covalently joined together by disulfide bonds and each light chain is joined to a heavy chain by disulfide bonds. IgM is characterized by the same basic structure as IgG, in multimeric form. Myeloma cells frequently secrete light chain monomers or dimers, sometimes termed myeloma proteins or Bence-Jones proteins, some of which have capacity to bind an antigen. The light and heavy chains of normal antigens are synthesized by the general mechanisms of protein synthesis in cells. The heavy and light chains are separately synthesized and subsequently joined together.

Chemical reassortment of antibody chains has been attempted in the prior art. Early attempts by Stevenson, G. T., et al (*Biochem.J.* 108, 375 (1968)), yielded only a minor proportion of heterologous associations. More recently, Peabody, D. S., et al, *Biochemistry* 19, 2827 (1980) demonstrated specific heterologous association of light chains from different myeloma sources. The hybrid molecules showed binding affinity for a ligand which one, but not both, of the parent molecules could bind. Heterologous association of heavy with light chains, or of heavy-light pairs, was not reported. Raso, V., *Cancer Res.* 41, 2073 (1981) has reported construction in vitro of antibody fragments ($F(ab')_2$ fragments) with binding affinity for two ligands. The reported procedure required partial degradation of the antibody molecules with a pepsin prior to reassortment of the fragments, such that the resulting dual-specificity binding proteins were fragments of antibody molecules.

The use of monoclonal antibodies for a variety of therapeutic purposes has been suggested. A particularly attractive application is for specifically targeted delivery of drugs to specific tissues or cell types, including tumors. For example, Gulliland, et al, *Proc. Nat. Acad. Sci. USA*, 77, 4539 (1980) have reported making chemical conjugates of a monoclonal tumor antibody with diphtheria toxin. The specific binding of the monoclonal antibody to the target cells makes it possible to deliver a specific drug, inhibitor or toxin to the desired cells while minimizing any interaction with other cells. Such techniques have depended upon chemical coupling reactions to conjugate the drug or toxin with the monoclonal antibody, with attendant disadvantages of loss of activity, reduced specificity and potential unwanted side reactions. Therefore it would be greatly advantageous to provide a targeted delivery system useful in conjunction with agents which need not be chemically coupled to an antibody molecule.

SUMMARY OF THE INVENTION

The present invention provides novel, recombinant monoclonal antibodies (hereinafter RMA) that are bifunctional in the sense of having binding affinities for two different antigens within a single antibody molecule. A RMA may bind its antigens simultaneously or sequentially. A RMA is characterized by any functional test which depends upon the binding of two different antigens by the same antibody, for example, by the ability to bind sequentially to each of two affinity chromatography columns, one bearing a first immobilized antigen and the other bearing a second immobilized antigen.

RMAs are produced by novel cell types constructed for the purpose. One such cell is termed a "quadroma" herein, and is formed by somatic cell fusion of two hybridomas, each parental hybridoma producing a monoclonal antibody specific for one of the two antigens. Another such novel cell type is termed "trioma" herein, and is formed by fusion of a hybridoma and a lymphocyte, each producing antibodies against one of the two antigens. The light and heavy chains of both parental types will be synthesized in quadroma and trioma cells. If light and heavy chains of both kinds are made in equivalent amounts and combined randomly, at least one-eighth of the antibodies produced by IgG-producing cells will be bifunctional RMAs. From IgM-producing cells, essentially all antibodies produced will be bifunctional in the sense of having at least one binding site for each of the two antigens.

The construction of triomas and quadromas depends on use of a selection system to distinguish the desired fusions from self-fused and non-fused parental cell types. Most of the selection systems disclosed herein depend upon the construction or isolation of mutant hybridomas which are, in themselves, believed to be novel. The selection system is designed to permit selective growth of hybrids of the two parental cell types, a high proportion of which will produce RMAs.

Quadromas and triomas are cloned by procedures essentially similar to those for cloning hybridomas, except that the cultures will be screened for ability to bind two antigens in a single clone. Further analysis of the bifunctional nature of the RMAs themselves will be carried out by two-stage affinity chromatography or by analytical techniques involving a solid-phase immobilized antigen to facilitate separation of monofunctional from bifunctional molecules.

The potential uses for quadromas, triomas and recombinant monoclonal antibodies are manifold. These include analytical and diagnostic techniques, targeted delivery of biological and pharmacologic agents to specific cells and the identification and localization of specific antigens, receptors and cell surface substances. The use of RMAs is advantageous since binding affinity and specificity are unaffected by prior chemical treatment used to covalently attach some sort of tag to a monofunctional antibody molecule. Further, the use of RMAs permits sequential administration of a dye, drug or tracer compound, thereby expanding the scope of utility of prior art techniques. For example, the RMA may be bound to the first antigen, such as a target cell, in one step, and the second antigen, such as a drug or tracer substance, bound to the complex in a subsequent step. The subsequent step could be carried out under different conditions than the first step.

RMAs may be converted to F(ab')$_2$ fragments of dual specificity, for therapeutic use where rapid renal clearance of the antibody after administration is desired.

DETAILED DESCRIPTION OF THE INVENTION

An initial step in the production of recombinant monoclonal antibodies is immunization to provide a population of spleen cells producing the desired antibody. Immunization may be accomplished by conventional in vivo immunization of an experimental animal, such as a mouse, from which spleen cells are subsequently obtained. Alternatively, there are advantages to direct in vitro immunization of spleen cells in culture, such as the method described by Luben, R. A., et al, *Proc.Second Int. Lymphokine Workshop*, Academic Press, New York, N.Y. (1979). In vitro immunization has the advantages that a large proportion of immune spleen cells may be obtained in less time than required by conventional immunization, and that human cell lines may be immunized without subjecting a human to immunization with potentially harmful substances. A further advantage is that several antigens can be used at once to prepare hybridomas against several antigens simultaneously.

A variety of myeloma cell lines are available for hybridization with mouse or human cells. Many myeloma strains produce light chain monomers or dimers, and frequently, although not always, hybridomas derived from such cells continue to excrete these proteins. Nonproducing myeloma strains are preferred for most hybridizations, to avoid production of myeloma proteins by the hybridoma. It is further preferred to use a hybridoma bearing a genetic selection marker to enable the investigator to selectively grow only the desired hybrids. A common selection system known in the prior art utilizes a mutant parent resistant to 8-azaguanine. Such mutants are unable to grow in medium containing hypoxanthine, aminopterin and thymidine (HAT medium). 8-azaguanine resistant mutants lack a functional hypoxanthine phosphoribosyl transferase (HPRT). Such cells are unable to grow in the presence of aminopterin. In conventional hybridoma technology, an 8-azaguanine resistant myeloma strain is commonly used. After fusion, hybrid cells receive a functional HPRT gene from the spleen cell parent and are therefore able to grow in HAT medium, while the parental myeloma cells and myeloma-myeloma fusions die. Parental spleen cells and spleen-spleen hybrids do not replicate in culture, so that no selection against them is required. Myeloma strains lacking functional thymidine kinase (TK$^-$) are also known. Such strains also fail to survive in HAT medium.

Screening for antibody production is a critical step in hybridoma technology. Antibody functional attributes vary widely. Monoclonal antibodies may differ from one another in binding affinity, ability to precipitate antigen, ability to inactivate antigen, ability to fix complement and degree of crossreactivity. Preferably, the screening assay should be designed to depend upon, or approximate, the functional properties desired of the antibody to be produced. However, the assay must be sufficiently simple to permit the screening of large numbers of samples. Although the techniques in the prior art vary, the screening process is carried out in two cycles. In the first, the fusion culture is subdivided to permit growth of a large number of cultures, each arising from a relatively small number of hybridomas. For example, if cells at a concentration of $10^5$/ml are fused, yielding 10% total hybridomas ($10^4$ hybridomas/ml), 10 $\mu$l samples of such culture will contain on the average 100 hybridomas per sample. If the desired antibody occurs at a frequency of 1 in 10³, approximately 10 of 100 cultures inoculated with 10 μl each will be positive for the desired antibody. Positive cultures are then subdivided again, this time at the level of 0.1 to 0.3 hybridoma cells per culture on the average, to ensure that each culture is a clone (all cells therein derived from a single parent cell, reproducing mitotically). Inasmuch as subculturing and screening procedures are labor-intensive, various techniques have been developed to simplify the procedures. For example, if an antigen can be labeled with a fluorescent marker, individual cells producing the desired antibody can be separated by commercially available cell sorting equipment, such as the fluorescence-activated cell sorter (FACS) manufactured by Becton Dickinson, Inc., Palo Alto, Calif. The instrument is capable of selectively separating cells bearing the fluorescent marker from a mixed population of cells. Another useful procedure is the soft agar cloning technique described by Sharon, J., et al, *Proc.Nat-.Acad.Sci.USA* 76, 1420 (1979), which permits in situ testing for antibody production.

Procedures for obtaining triomas and quadromas are similar in principle, but more complex in practice since additional techniques for selection must be employed. For example, if the initial hybridoma is isolated by HAT selection, it will have functional HPRT and will therefore not be a suitable parent in a second round of fusion unless another selection marker is present or the hybridoma is again mutated and selected for 8-azaguanine resistance. In the case of the fusion of two hybridomas to form a quadroma, there must be means available to select against both parental cell lines. Three selection systems are described, as representative of the techniques and principles which are generally operative. Other selection techniques, based on other forms of genetic modification or biochemical inhibition may be employed, as will be readily apparent to those skilled in the art.

HAT selection may be employed using two separate genetic markers, both of which convey sensitivity to aminopterin. Where one parent hybridoma lacks functional HPRT (HPRT−) and the other lacks functional thymidine kinase (TK−), only quadromas produced by fusion of the two parent hybridomas will survive in HAT medium. HPRT− mutant hybridomas may be obtained by selection for growth in the presence of 8-azaguanine or 6-thioguanine, presented at progressively higher concentrations up to 100 μM. TK− mutants may be selected by growth in progressively increasing concentrations of 5-bromo-2′-deoxyuridine. The techniques for selection of HPRT− and TK− mutant hybridomas are essentially similar to those previously described for selection of such mutants in conventional cells (Littlefield, J. W., *Proc.Nat.Acad.Sci.USA* 50, 568 (1963).

Selection may also be based on the use of mutant hybridomas resistant to ouabain. Ouabain is an inhibitor of the Na+, K+-dependent ATPase essential for active transport in normal cells. Ouabain-resistant cells are able to survive levels of ouabain which kill normal, ouabain-sensitive cells. Ouabain-resistance may be used as a selection marker by itself, or in combination with other markers. In a preferred embodiment, a single hybridoma is selected for both ouabain resistance and resistance to either 8-azaguanine (HPRT−) or 5-bromo-2′-deoxyuridine (TK−). The double mutant hybridoma is used as a universal fuser, to combine with any desired hybridoma to produce a quadroma which can be selectively grown in HAT-ouabain medium. In such medium the universal fuser parent hybridoma will die since, with either TK− or HPRT− mutations, it cannot grow in HAT medium. The other parent hybridoma is killed because it lacks resistance to ouabain. Any quadroma which has retained a functional TK or HPRT gene while remaining ouabain-resistant will grow selectively in HAT-ouabain medium. The universal fuser is especially advantageous because many of the contemplated uses of RMAs employ a single common binding specificity for one of the two binding affinities of the antibody molecule. For example, the use of a recombinant monoclonal antibody in an enzyme-linked immunosorbent assay (ELISA) for a variety of different antigens would require a common binding specificity for the indicator enzyme. Similarly, targeted drug delivery systems can employ a common specificity site for binding the therapeutic agent and a variable specificity for binding tissue-specific or cell-specific antigens.

While the foregoing selection techniques require the construction of mutant hybridoma strains and depend upon the retention of certain genes in the quadroma fusion product, a third technique, based upon irreversible biochemical inhibitors, requires no mutation. An irreversible biochemical inhibitor is one which binds chemically and which exerts a specific inhibitory action in a cell with which it has been treated. A fusion product combining parent cells treated with two separate inhibitors will be uninhibited due to complementation. For example, one parent hybridoma is treated with diethylpyrcocarbonate, the other with iodoacetamide. Both parent strains ultimately die, but fusions between the two survive (see Wright, W. E., *Exptl. Cell Res.* 112, 395 (1978)).

The techniques of selection and cloning for triomas and quadromas applicable to conventional hybridomas are also applicable for the quadromas and triomas of the present invention. Preferably, a fluorescence-tagged antigen is employed in the detection and cloning systems. Individual cells which bind a fluorescent antigen can be separated by a fluorescence-activated cell sorter. Such instruments are capable of depositing single cells in individual microtitre wells, thereby greatly reducing the labor associated with conventional selection and cloning.

The detection of trioma and quadroma clones producing antibodies with binding specificity for two different antigens is strong presumptive evidence of the production of RMAs. Further steps are necessary, in most instances, to isolate RMA free from other antibodies which may be produced by the same cell including, for example, antibody molecules having a single specificity, inactive antibody molecules and myeloma proteins. True RMA molecules are immunoglobulins having a dual binding specificity. RMAs are specifically purified by two stages of affinity chromatography in series. The first stage entails the specific binding to an affinity column bearing immobilized first antigen. Antibody molecules which fail to bind at the first stage pass through the column and are discarded. Antibodies binding to the first column are then eluted with a chaotropic ion buffer and applied, in the second stage, to a second affinity column bearing the second antigen. Only recombinant monoclonal antibodies which can bind to either column are bound to the second. After appropriate elution steps, the recombinant monoclonal antibody is obtained in essentially pure form.

The existence of RMAs may be detected and quantified by a solid-phase assay, without resorting to two-stage affinity chromatography. For example, the first antigen is immobilized by binding to a solid phase support material. A variety of such solid phase supports and binding techniques are well known in the art. The antibody preparation is then incubated with the solid-phase support to permit binding of any antibody having affinity for the immobilized antigen. The support is then washed to remove non-binding antibody and then incubated with the second antigen, which is tagged with an appropriate marker, such as a radioisotope, fluorescent ligand or conjugated enzyme. While both RMAs of dual specificity and conventional antibodies against the first antigen are capable of binding the immobilized first antigen, only the RMAs will be capable of binding the tagged second antigen. All antibodies capable of binding the second antigen but not the first are removed by the washing step, and therefore do not interfere with the assay. Therefore, both qualitative and quantitative measurement of a recombinant monoclonal antibody in the presence of antibodies of some other specificity is accomplished.

Some of the uses contemplated for RMAs are next described.

A hybridoma providing monoclonal antibody to a tumor-specific antigen is fused with a hybridoma making monoclonal antibody to the toxic subunit of the 60,000 m.w. toxin from *Ricinus communis*. The quadroma will produce RMA which can be armed with toxin and used to bind to tumor cells which would internalize the toxin, which would kill the tumor cells.

A hybridoma making monoclonal antibody to a tumor-specific antigen is fused with a hybridoma making monoclonal antibody to trinitrophenol (TNP). TNP can be covalently bound to amino groups on the exterior surface of liposomes. The liposomes can be used for drug delivery, specifically to the tumor cell, since liposomes can be made to encapsulate chemotherapeutic drugs. The liposomes would be coated with RMA which binds to TNP and the RMA would also bind to the tumor, resulting in fusion of the liposomes with tumor cells, and introduction of the drug into the tumor cells. Alternatively an RMA for a cell-specific antigen and a hapten, such as a drug or hormone may be employed for specific and direct delivery of the hapten to the desired cell.

A hybridoma making monoclonal antibody to a hormone e.g., B subunit of human chorionic gonadotropin, drug or tumor-specific antigen is fused to a hybridoma producing monoclonal antibody to a radioactive hapten labeled to high specific activity with a radioactive isotope. The quadroma will produce RAM which can be armed with radioactivity. Such RMA may be used for assay, tumor localization or therapy. Choice of isotope depends upon the nature of the intended end use. A $\gamma$-emitting isotope may be used for immunoassay of drugs, hormones and other haptens in body fluids, tissue samples, urine and the like. If the tumor-specific antigen, hormone or drug is bound to a solid phase, the RMA could be used in a one-step competition radioimmunoassay. Gamma-emitting isotopes are also useful for tumor localization. High-energy $\alpha$-emitting isotopes are especially useful for therapeutic purposes because of the high energy and short path of $\alpha$-radiation in tissue. Beta-emitting isotopes may be used for assay purposes as well, but require counting equipment not commonly found in a clinical laboratory.

The hybridoma producing monoclonal antibody to the antigen of diagnostic interest in the preceding paragraph is fused with a hybridoma producing monoclonal antibody to the enzyme horseradish peroxidase. The quadroma will produce RMA which can be used for a one-step enzyme-linked immunosorbant assay (ELISA).

A hybridoma producing monoclonal antibody to a tumor-specific antigen is fused with a hybridoma producing monoclonal antibody to a fluorescent probe. The quadroma will produce RMA which can be used for the fluorescent microscopic detection of tumor cells in tissue sections, or for enumeration of tumor cells in cellular suspensions using flow microfluorimetry (FMF).

The term "tumor-specific antigen" as used herein will be understood to connote an antigen characteristic of a particular tumor, or strongly correlated with such a tumor. However, the current understanding in the art with respect to tumor-specific antigens is that they are not necessarily unique to the tumor tissue, or that antibodies to them may cross-react with antigens of normal tissue. Even where tumor-specific antigens are not unique to tumor cells, it frequently occurs that, as a practical matter, antibodies binding to tumor-specific antigens are sufficiently specific to tumor cells to carry out the desired procedures without unwarranted risk or interference due to cross-reactions. Many factors contribute to this practical specificity. For example, the amount of antigen on the tumor cell may greatly exceed the amount found on normal cells, or the normal cells bearing cross-reactive antigen may be localized remote from the tumor. The antigen in the normal state may only be partially cross-reactive with the tumor-specific antigen. Sometimes, a product specific to the cell-type constituting the tumor may serve as a practical tumor-specific antigen. For example the antibody produced by the lymphocytic leukemia cells may itself be used as an antigen, against which an "anti-idiotype" antibody may be selected to bind specifically to such cells. Therefore the term "tumor-specific antobody" relates herein to a specificity of practical utility, and is not intended to denote absolute specificity or to imply an antigen unique to the tumor.

Further, it will be understood that cells other than tumor cells may have cell-specific antigens characteristic, or strongly correlated with a given type cell. Given tissues may have tissue-specific antigens which are characteristic, or predominantly associated with a given tissue. Cell-specific and tissue-specific antigens are also useful for producing RMAs capable of binding preferentially, if not exclusively, to desired cells and tissues.

The following examples illustrate the techniques applied to the production of a quadroma producing an RMA. The described techniques can be applied, essentially as described, to prepare quadromas and produce recombinant monoclonal antibodies capable of binding any desired pair of antigens.

While most RMAs will have binding affinities for two different antigens, it will be understood that RMAs binding two different epitopes on the same antigen could be prepared from appropriately selected quadroma or trioma clones. The significant variations in procedure for preparing other RMAs will lie in the nature of the antigen used to immunize, the screening test used to detect antibody production by the relevant hybridomas, triomas and quadromas and in the purification methods employed. The screening assay is especially significant, since it is at this stage that one selects for desired antibody properties in addition to binding affinity, e.g., whether the antibody precipitates the antigen, binds complement, cross-reacts with other antigens, and the like. Variations in technique of the type known in the art and understood by those of ordinary skill to be functional equivalents of those disclosed herein may be substituted as desired, for convenience or for optimization of yield, or to simplify or improve the cost-effectiveness of the overall procedure.

EXAMPLE 1

The following antigens are prepared in order to produce recombinant monoclonal antibody having dual binding affinity for two fluorescent haptens, fluorescein and rhodamine: fluorescein isothiocyanate-conjugated bovine serum albumin (F-BSA), fluorescein isothiocyanate labeled ovalbumin (F-OVA), rhodamine isothiocyanate-conjugated bovine serum albumin (R-BSA), and rhodamine isothiocyanate-conjugated ovalbumin (R-OVA). Fluorescein and rhodamine are chosen as haptens because they are readily assayed by fluorescence and they may be assayed in the presence of one another because their excitation and emission maxima are substantially different from one another. The use of the same hapten coupled to two different proteins makes it possible to distinguish between antibodies directed against the hapten and antibodies directed against the protein to which it is conjugated. For example, where F-BSA is used for immunization, screening is carried out with F-OVA. Only antibodies with binding affinity for the fluorescein moiety are detected in the screening assay. The isocyanate derivatives of fluorescein and rhodamine are commercially available, for example, from Sigma Chemical Co., St. Louis, Mo.

To carry out the coupling reaction, 50 mg protein in 10 ml of 0.1M NaHCO$_3$, pH 9, are mixed with 5 mg of the desired isothiocyanate derivative and incubated for 30 minutes at room temperature with continuous gentle stirring. The product, after filtration through glass wool to remove precipitated protein and insoluble unreacted isothiocyanate, is chromatographed on Sephadex G-25 (trademrk, Pharmacia, Inc., Uppsala, Sweden) in phosphate buffered saline (10 mM Na-phosphate pH, 7.4, 0.15M NaCl) to separate the derivatized protein from the unreacted product and to change the buffer system. The peak of derivatized protein is identified visually, and elutes in the volume of buffer equivalent to the void volume of the column. The derivatized protein is used without further purification for immunization and testing.

EXAMPLE 2

Immunization

Immunization in vivo is carried out using a method based on that of Vaitukaitis, J., et al, *J. Clin. Endocrin.* 33, 988 (1971). Antigen, 100 ng, in an emulsion of complete Freund's adjuvant and physiological saline in equal volumes is injected intradermally in 20 sites. After one week a second injection of the same antigen preparation is introduced into the granulomas resulting from the first injection. Two weeks later, 100 ng of antigen is injected using incomplete Freund's adjuvant:saline (1:1) subcutaneously in four sites over the shoulders and hips. One week later, a sample of blood is obtained from the tail and assayed for antibodies. The animal is now boosted intravenously with 1 μg of antigen per injection for four days in a row. This treatment maximizes the number of lymphoblast cells present in the spleen, so that the frequency of antigen-specific hybridomas formed after the fusion step is increased.

The procedure for immunization in vitro is based upon a technique described by Luben, R. A., et al, *Proc. Second Int. Lymphokine Workshop*, Academic Press, New York, N.Y. (1979).

The spleen of a non-immunized adult BALB/c mouse is removed by sterile technique and a single-cell suspension of spleen cells is prepared. The cells are diluted to 20 ml with complete Dulbecco's modified Eagle's medium (hereinafter DMEM, commercially available from Grand Island Biological Company, Grand Island, N.Y.), containing 30 μg to 1,000 μg of antigen and 10 ml of thymoctye-conditioned medium is added.

Thymoctye-conditioned medium is prepared from the thymocytes of three 10-day-old mice or from a mixed thymocyte culture from adult mice. Thymocytes from BALB/c mice and those from a strain differing at the major histocompatibility locus (e.g., C57 Black) are co-cultivated at 2 to 4×10$^6$ thymocytes/ml in complete DMEM. After 48 hours incubation at 37° C., the cells and debris are centrifuged and the medium is aspirated and stored frozen in 10 ml aliquots at −70° C.

The mixture of non-immune spleen cells, antigen and thymocyte conditioned medium is placed in a 75 cm$^2$ flask and left untouched in a tissue culture incubator for five days at 37° C. After five days, successful immunization yields numerous large lymphoblasts observable by phase contrast microscopy. The cells are then ready for fusion.

EXAMPLE 3

Lympocyte-myeloma fusion and isolation of hybridomas

A myeloma strain, designated SP2, described by Shulman, M., et al, *Nature* 276, 269 (1978) is chosen for fusion. The SP2 cell line is characterized as a non-producer of myeloma protein and is 8-azaguanine resistant, due to defective HPRT activity. The SP2 cell line has been widely disseminated, and may be obtained, for example, from Professor Klinman at Scripps Clinic and Research Foundation, La Jolla, Calif.

The fusion medium contains polyethylene glycol, 1,540 M.W. at 47% (v/v) and dimethyl sulfoxide at 7.5% (v/v) in serum-free DMEM. Polyethylene glycol induces cell fusion, as described by Pontecorvo, G., *Somatic Cell Genet.*, Vol. 1, 397 (1975) Dimethyl sulfoxide reportedly enhances fusion frequency, possibly by lowering the membrane phase transition temperature, as described by Norwood, T. H., et al, *Somatic Cell Genet.*, Vol. 2, 263 (1976).

For spleen cells immunized in vivo, a single cell suspension is made from a hyperimmune spleen as described for the immunization in culture. SP2 myeloma cells in exponential growth phase (30 ml, 5–8×10$^5$ cells/ml) are transferred to a 50 ml conical polypropylene centrifuge tube and the spleen cell suspension (5 ml) is added. For spleen cells immunized in culture, the cells are harvested after dislodging adherent lymphoblast cells, centrifuged, and the medium removed. The SP2 cells (30 ml) are added as above. With either preparation, the cells are washed three times with 50 ml of serum-free DMEM by centrifugation. The pellet from the third wash is resuspended in 1 ml of fusion medium just removed from a 37° C. waterbath. The medium is added over one minute and the cells continuously stirred with the pipet tip. Stirring is continued for another minute. Two ml of serum-free DMEM at 37° C. are added over the next three minutes with continuous stirring. Seven ml of 37° C. DMEM containing 10% rabbit serum is added over the next three minutes with stirring. The cells are centrifuged and resuspended in 10 ml complete medium containing HAT selection chemicals and feeder cells and distributed into 96 wells of a microtitre plate.

Feeder cells are peritoneal exudate cells obtained after intraperitoneal injection of 0.5 ml pristane (2,6,10,14-tetramethyl-pentadecane). After four days, cells are collected by washing out the peritoneal cavity of the treated mice. The yield is consistently $2-4 \times 10^7$ cells per mouse.

Antibody producing cells are directly cloned using the fluorescence-activated cell sorter. Positive cells will bind the fluorescent probe of the instrument and be separated from negative cells. The probe is obtained from fluorescent hapten coupled to a different protein from that used in the immunization. For example, if F-BSA or R-BSA is used for immunization, F-OVA or R-OVA will be used as a probe, to avoid selection of hybridomas producing antibody against the protein.

An alternative screening procedure, suitable for non-fluorescent antigens, is based on enzyme-linked immunosorbant assay (Saunders, G. C., *Immunoassays in the Clinical Laboratory*, pp. 99–118 (1979)).

To detect antibodies to soluble antigen, 50 µl/well of 10–100 µg/ml antigen in water are added to polystyrene 96 well plates and they are allowed to dry in a 37° C. incubator. Immediately before use, the plates are washed three times with 10 mM $Na_2HPO_4$ in 150 mM NaCl (PBS-9). To screen antibodies for reactivity with cell surface components the cells are bound using an immobilized lectin. Concanavalin A is covalently bound to the polystyrene wells using a water-soluble carbodimide (Reading, C. L., et al, *J. Natl. Cancer Inst.* 64, 1241 (1980)). The plates are washed six times with PBS-9 and cells are added to each well $(1-2 \times 10^5)$ in 100 µl complete DMEM. The plates are kept at 37° C. for one to two hours to allow the cells to attach; after that the plates are washed six times with PBS-9 and 50 µl of fresh 1% formaldehyde in PBS-9 is added to each well. The plates are kept for 15 minutes at room temperature and then washed six times with PBS-9 and used immediately.

From each hybridoma culture, 50 µl of medium is transferred to the antigen containing wells. The samples are incubated at room temperature for 30 minutes and the plates are washed 10 times with 0.05% Triton-X-100 (trademark, Rohm & Haas Company, Nutley, N.J.) in water. Enzyme-conjugated anti-mouse immunoglobulin (Cappel Laboratories, Cochranville, Pa.) is diluted into 10 mM $Na_2HPO_4$, 0.05M NaCl, 0.5% (v/v) Triton-X-100 containing 50 µg/ml bovine serum albumin.

The conjugate (50 µl) is added to each well and incubated for 15 minutes at room temperature. The plates are washed 10 times with 0.5% (v/v) Triton-X-100, 100 µl of substrate is added. The chromogenic substrate 2,2'-azino-di-(3-ethyl)-benzthiazoline sulfonic acid (ABTS) is used as described by Saunders, supra. The colored enzyme product is quantitated by measuring the optical density at 414 mM.

Cells from cultures producing the desired antibody are counted and diluted to yield 30–50 viable hybridoma cells/ml of complete HT medium (DMEM containing $10^{-3}$M hypoxanthine, and $3 \times 10^{-4}$m thymidine).

A portion of 0.1 ml of the suspension is pipetted into each well of a 96 well microtitre plate containing $1.2 \times 10^5$ peritoneal exudate feeder cells. Each well contains on the average 3–5 hybridoma cells per well.

The cultures are incubated in a tissue culture incubator at 37° C. for seven days, following which 0.1 ml complete HT medium is added to each well. After an additional 14–21 days' incubation, the clones are dense and ready for screening, either by the ELISA procedure or by measurement of fluorescent quenching due to antibody binding of added fluorescent hapten. For specificity controls, antibodies reactive with fluorescein should not bind rhodamine, and vice versa. The six strongest positive cultures are transferred to larger wells, and are re-assayed after incubation to allow the cultures to again become dense. A portion of the cells from the strongest two cultures are re-cloned by limiting dilution, ~0.3 cells per well (using a feeder layer). The remainder of the cells in the two strongest positive cultures are incubated in additional medium to increase their numbers and stored frozen.

When the limiting dilution clones have reached adequate cell density, the wells with a single clone present are assayed. Six positive clones are transferred to larger wells, again incubated to increase their numbers, and stored frozen. The two strongest wells are examined for stability by another round of limiting dilution cloning. The FACS is useful in these selection and recloning steps, in the manner previously described. Since these processes are labor-intensive, the use of the cell sorter at any stage where applicable is advantageous. Clones which yield greater than 90% positive clones are considered stable. Clones which yield less than 90% positive clones are re-cloned until stability is achieved.

EXAMPLE 4

Quadroma Formation

The first step in quadroma formation is the selection of mutant hybridoma strains suitable for preferentially growing quadroma fusion products in the presence of the parent hybridomas. In this example, the hybridoma strain producing antibody against fluorescein is further modified to 8-azaguanine and ouabain resistance. The modified hybridoma is used as a universal fuser, as described, supra.

Selection for 8-azaguanine resistance involves a process of adaptive growth in gradually increasing concentrations of the inhibitor, beginning with inhibitor concentrations of about 1 µM. Cells grown for several generations are then transferred to 3 µM 8-azaguanine for an additional period of growth for several generations. The process is reiterated, with progressive increments of inhibitor, until a viable strain growing in the presence of 100 µM 8-azaguanine is obtained. The procedure selects mutants arising spontaneously or by 8-azaguanine induced mutation, which lack functional HPRT activity. The 8-azaguanine resistant hybridoma strain is then made resistant to ouabain inhibition by a similar process of adaptive growth, using essentially the method described by Baker, R. M., et al, *Cell* 1, 9 (1979).

Equal numbers of anti-fluorescein producing double mutant hybridomas, prepared as described, and antirhodamine producing hybridomas are fused, following essentially the procedure of Example 3. The yield of quadromas producing antibodies against both antigens is higher, per stable fusion, than for conventional fusions, since every parental cell is of the desired type. After the fusion step is complete and the cells dispensed in microtitre plate wells, they are incubated in the presence of HAT medium (DMEM containing $3\times10^{-6}$M thymidine, $4\times10^{-7}$M aminopterin, and $3\times10^{-5}$M hypoxanthine) containing $10^{-3}$M ouabain. As previously described, both parental hybridoma strains are killed by growth in HAT-ouabain medium, while quadromas which have retained functional HPRT and the ouabain resistance mutation survive and grow.

After selection, quadromas which bind both antigens simultaneously are cloned in individual microtitre wells using the single-cell deposition attachment for the fluorescence-activated cell sorter. The single cells will develop into dense cultures within 10-14 days.

Alternatively, quadromas are detected and cloned by plating in soft agar medium. After 10-14 days' growth, the clones which appear are tested in situ by the solid phase assay described by Sharon et al, supra.

Replicate tests are required, first with one antigen, then with the other. Clones which react with both antigens contain the desired quadroma. Alternatively, screening may be carried out by allowing quadromas to bind to a surface coated with one antigen, the testing for ability to bind with the other antigen.

As previously described for hybridomas, the most active and stable clones are re-cloned to ensure stability. Clones which yield greater than 90% positive clones are considered stable, while those yielding less than 90% are recloned until stability is achieved. Quadroma clones producing presumptive RMAs are those which produce antibody binding both of the immunizing antigens, fluorescein and rhodamine.

EXAMPLE 5

Preparation and purification of recombinant monoclonal antibody

RMAs are isolated, either from the supernatant of quadroma cultures or from ascites from a mouse injected with quadroma cells interperitoneally. In the latter case, BALB/c mice are pretreated by interperitoneal injection of 0.5 ml pristane. An injection of $1-2\times10^6$ quadroma cells of a stable clone are injected intraperitoneally. Ascites tumors are evident by day 10 to 21, and the ascites fluid is collected when the peritoneal cavity becomes distended. Cells are removed by centrifugation and antibody is precipitated with 60% saturated ammonium sulfate. The antibody is then dialyzed and frozen. The yield is usually about 30-50 mg of antibody per mouse.

Recombinant monoclonal antibodies are further purified from the antibody preparation by two stages of affinity chromatography. In the first column, F-BSA is coupled to CNBr-activated Sepharose 4B (trademark, Pharmacia Fine Chemicals AB, Uppsala, Sweden) using standard coupling procedures as described by March, S. C., et al, *Anal. Biochem.* 60, 149 (1974). The second column is packed with R-BSA coupled to CNBr-activated Sepharose 4B. The columns are equilibrated with PBS-9 and the antigen preparation is applied to the first column and eluted with 2-3 column volumes of PBS-9. The first column is then eluted with PBS-9 containing 3M potassium isothiocyanate. Eluted protein is dialyzed against PBS-9 and applied to the second column, which is eluted in the same manner as the first. Protein recovered from the second column after potassium isothiocyanate elution is recombinant monoclonal antibody, which has two distinct combining sites per molecule, one for fluorescein and one for rhodamine. The RMA preparation is dialyzed, concentrated and stored frozen.

The foregoing specification describes the formation of novel cell types, quadromas and triomas, capable of producing recombinant monoclonal antibodies, a heretofore unknown molecular species of antibody having binding affinities for two different antigens and capable of binding both antigens simultaneously. The techniques for producing such new materials have been described in detail, particularly with reference to specific embodiments included by way of example. It will be understood that the products and techniques of the present invention are of far-reaching significance and include a wide range of RMA types combining any pair of antigenic specificities on a single antibody. It will be further understood that many variations and modifications of the techniques employed herein are available to those of ordinary skill in the relevant art, and that such variations and modifications are contemplated as being within the scope of the invention.

What is claimed is:

1. A quadroma cell, wherein said quadroma cell is the fusion product of a first hybridoma cell which produces an antibody having specific binding affinity to a first desired antigen and a second hybridoma cell which produces an antibody having specific binding affinity for a second desired antigen, and wherein said quadroma cell produces a recombinant monoclonal antibody having specific binding affinity for both said first and said second desired antigens.

2. The quadroma cell of claim 1, wherein one of the two antigens is a tumor-associated antigen.

3. The quadroma cell to claim 1, wherein one of the two antigens is a cell-specific antigen.

4. The quadroma cell of claim 1, wherein one of the two antigens is a tissue-specific antigen.

5. The quadroma cell of claims 1, 2, 3 or 4, wherein one of the two antigens is an enzyme.

6. The quadroma cell of claims 1, 2, 3 or 4, wherein one of the two antigens is a hapten.

7. The quadroma cell of claims 1 or 2 wherein one of the two antigens is a *Ricinus communis* toxin.

8. The quadroma cell of claims 1 or 2, wherein one of the two antigens is specific for trinitrophenol.

9. The quadroma cell of claim 6, wherein the hapten is radioactively-labelled.

10. The quadroma cell of claim 1, wherein one of the two antigens is human chorionic gonadotropin and the other antigen is a hapten.

11. The quadroma cell of claim 1, wherein one of the two antigens is human chorionic gonadotropin and the other antigen is horseradish peroxidase.

12. The quadroma cell of claims 1 or 2, wherein one of the two antigens is fluorescein.

13. The quadroma cell of claim 1, wherein said antibody is an IgM molecule.

14. The quadroma cell of claim 1, wherein said antibody is an IgG molecule.

15. A trioma cell, wherein said trioma cell is the fusion product of a hybridoma cell which produces an antibody having specific binding affinity to a first desired antigen and a lymphocyte which produces an antibody having specific binding affinity to a second desired antigen, and wherein said trioma cell produces a recombinant monoclonal antibody having specific binding affinity for both said first and said second desired antigens.

16. The trioma cell of claim 15, wherein one of the two antigens is a tumor-associated antigen.

17. The trioma cell of claim 15, wherein one of two antibodies is a cell-specific antigen.

18. The trioma cell of claim 15, wherein one of the two antigens is a tissue-specific antigen.

19. The trioma cell of claims 15, 16, 17 or 18, wherein one of the two antigens is an enzyme.

20. The trioma cell of claims 15, 16, 17 or 18, wherein one of the two antigens is a hapten.

21. The trioma cell of claims 15 or 16, wherein one of the two antigens is *Ricinus communis* toxin.

22. The trioma cell of claims 15 or 16, wherein one of the two antigens is specific for trinitrophenol.

23. The trioma cell of claim 20, wherein the hapten is radioactively-labelled.

24. The trioma cell of claim 15, wherein one of the two antigens is human chorionic gonadotropin and the other antigen is a hapten.

25. The trioma cell of claim 15, wherein one of the two antigens is human chorionic gonadotropin and the other antigen is horseradish peroxidase.

26. The trioma cell of claim 15, wherein one of the two antigens is fluorescein.

27. The trioma cell of claim 15, wherein said antibody is an IgM molecule.

28. The trioma cell of claim 15, wherein said antibody is an IgG molecule.

29. A method of producing a quadroma cell comprising: (A) fusing a first hybridoma cell which produces an antibody having specific binding affinity to a first desired antigen, to a second hybridoma cell which produces an antibody having specific binding affinity to a second desired antigen, and (B) selecting a quadroma cell which produces a recombinant monoclonal antibody having specific binding affinity for both said first and said second desired antigens.

30. The method of claim 29, wherein one of the two antigens is a tumor-associated antigen.

31. The method of claim 29, wherein one of the two antigens is a cell-specific antigen.

32. The method of claim 29, wherein one of the two antigens is a tissue-specific antigen.

33. The method of claims 29, 30, 31 or 32, wherein one of the two antigens is an enzyme.

34. The method of claims 29, 30, 31 or 32, wherein one of the two antigens is a hapten.

35. The method of claims 29 or 30, wherein one of the two antigens is *Ricinus communis* toxin.

36. The method of claims 29 or 30, wherein one of the two antigens is specific for trinitrophenol.

37. The method of claim 34, wherein the hapten is radioactively-labelled.

38. The method of claim 29, wherein one of the two antigens is human chorionic gonadotropin and the other antigen is a hapten.

39. The method of claim 29, wherein one of the two antigens is human chorionic gonadotropin and the other antigen is horseradish peroxidase.

40. The method of claims 29 or 30, wherein one of the two antigens is fluorescein.

41. The method of claim 29, wherein said recombinant monoclonal antibody is an IgM molecule.

42. The method of claim 29, wherein said recombinant monoclonal antibody is an IgG molecule.

43. A method of producing a trioma cell comprising: (A) fusing a hybridoma cell which produces an antibody having specific binding affinity to a first desired antigen, to a lymphocyte which produces an antibody having specific binding affinity to a second desired antigen, and (B) selecting a trioma cell which produces a recombinant monoclonal antibody having specific binding affinity for both said first and second desired antigens.

44. The method of claim 43, wherein one of the two antigens is a tumor-associated antigen.

45. The method of claim 43, wherein one of the two antigens is a cell-specific antigen.

46. The method of claim 43, wherein one of the two antigens is a tissue-specific antigen.

47. The method of claims 43, 44, 45 or 46, wherein one of the two antigens is an enzyme.

48. The method of claims 43, 44, 45 or 46, wherein one of the two antigens is a hapten.

49. The method of claims 43 or 44, wherein one of the two antigens is *Ricinus communis* toxin.

50. The method of claims 43 or 44, wherein one of the two antigens is specific for trinitrophenol.

51. The method of claim 48, wherein the hapten is radioactively-labelled.

52. The method of claim 43, wherein one of the two antigens is human chorionic gonadotropin and the other antigen is a hapten.

53. The method of claim 43, wherein one of the two antigens is human chorionic gonadotropin and the other antigen is horseradish peroxidase.

54. The method of claim 43, wherein one of the two antigens is fluorescein.

55. The method of claim 43, wherein said recombinant monoclonal antibody is an IgM molecule.

56. The method of claim 43, wherein said recombinant monoclonal antibody is an IgG molecule.

* * * * *